United States Patent [19]

Wenke

[11] Patent Number: 5,034,014

[45] Date of Patent: Jul. 23, 1991

[54] HAIR DYE COMPOSITION AND METHOD

[75] Inventor: Gottfried Wenke, Woodbridge, Conn.

[73] Assignee: Clairol, Inc., New York, N.Y.

[21] Appl. No.: 539,777

[22] Filed: Jun. 18, 1990

[51] Int. Cl.$^5$ .............................................. A61K 7/13
[52] U.S. Cl. ......................................... 8/408; 8/406; 8/409; 8/410; 8/415; 8/416
[58] Field of Search .................. 8/408, 409, 406, 410, 8/415, 416, 423, 424, 429

[56] References Cited

U.S. PATENT DOCUMENTS

| | | | |
|---|---|---|---|
| 3,957,424 | 5/1976 | Zeffren et al. | 8/416 |
| 4,904,275 | 2/1990 | Grollier | 8/408 |

FOREIGN PATENT DOCUMENTS 2057019 7/1980 United Kingdom .

Primary Examiner—Josephine Barr
Assistant Examiner—William S. Parks
Attorney, Agent, or Firm—Morton S. Simon

[57] ABSTRACT

An aromatic amine, or a cosmetically acceptable salt thereof, is reacted with an aromatic aldehyde in a reaction medium containing water. 2,6-dihydroxypyridine, or a cosmetically acceptable salt thereof, is reacted with hydrogen peroxide in a reaction medium containing water. The two reaction mediums are combined so that both reactions are carried out together on hair. Preferably, the two reactions are carried out together in the same reaction medium. pH is adjusted so that the pH of the common reaction medium is about 5 to 7. Surprisingly, substantially no cross reaction occurs between the two reactions on hair.

8 Claims, No Drawings

HAIR DYE COMPOSITION AND METHOD

The present invention relates to a new dyeing method. More particularly, it relates to a method for dyeing hair wherein the hair is treated with an aqueous solution containing an aromatic amine, an aromatic aldehyde, 2,6-dihydroxypyridine and an oxidizing agent, preferably, hydrogen peroxide, at a pH of about 5 to about 7, and for less than about 20 minutes.

U.S. Pat. Nos. 3,871,818 and 3,904,357 (Kinney et al) describe hair dyeing using a dialdehyde compound in combination with a nitrogen containing compound. However, the range of available precursors is limited and controlled variation of shades is difficult, if not impossible.

U.S. Pat. No. 3,158,542 (Kalopissis) discloses a hair dyeing method using the reaction of an aromatic diketone, i.e. substituted diacetyl benzenes, with an amine. According to patentee, development of the desired shade takes place in situ and provides good fastness. Useful dye precursors are, however, limited and expensive.

U.S. Pat. No. 4,391,603 (Rosenbaum et al) discloses a method of dyeing hair by application of a solution of certain aromatic aldehydes. Included among such aldehydes are aldehydes utilizable in the composition and method of the present invention.

The aldehyde solution ultimately contains a p-phenylenediamine derivative. The solution has an acid pH. According to patentee, the aldehydes are especially suitable for providing a yellow color.

British patent 2,057,019 (corresponding to German 2,932,489) and German 2,830,497 (both to Schwarzkopf) disclose benzaldehyde and derivatives thereof, which can be used in combination with any one of an oxidizing agent, a hair dye precursor, and a direct dye. A number of benzaldehyde compounds identified in these patents are utilizable in the compositions and method of the present invention. According to British patent 2,057,019, suitable dye precursors include p-phenylenediamine and derivatives thereof. The process of dyeing hair disclosed by these patents is optionally carried out in the presence of oxidants and other precursors employed in permanent hair dyeing. Color formation occurs by oxidization of the hydroxybenzaldehyde and is limited to the range yellow to brown. Dye removal from the hair is, however, only possible by harsh chemical treatments.

U.S. Pat. No. 3,231,471 describes the use of 2,6-dihydroxypyridine in oxidative hair dyeing compositions as a conventional oxidation dye coupler. It reacts with para disubstituted benzenes. From U.S. Pat. No. 3,231,471 one skilled in the hair dyeing art would expect that the 2,6-dihydroxypyridine would react on hair with an aromatic amine (which is substituted with amino or hydroxy in the para position) to produce typical oxidation dyes. For example, with p-phenylene diamine a red-violet color would be produced on hair and not the blue color it would typically produce in the absence of aromatic amine.

It is evident from the above discussion of the prior art that the Schiff base reaction between an amine and an aldehyde and/or ketone are known in the hair dyeing arts. Similarly, the oxidation of 2,6-dihydroxypyridine with peroxide is also known.

Surprisingly and unexpectedly, the present inventor has discovered that these two reactions take place on hair independently, substantially without the occurrence of expected cross reactions, when hair is exposed to a solution containing the aromatic amine, aldehyde, 2,6-hydroxypyridine and hydrogen peroxide. One skilled in the art would expect such cross reactions to take place. The fact that they substantially do not is indeed unexpected and surprising. More importantly, since expected cross reactions substantially do not take place, it is possible to obtain a hair dye that is a blend of the yellow to red colors provided by the Schiff base reaction and the blue color provided by oxidation of the dihydroxypyridine. Advantageously, the composite color produced by these dyes is shampoo fast while being readily removable by a short treatment with alkaline hydrogen peroxide.

If the cross reaction between 2,6-dihydroxypyridine and the aromatic amine had occurred in hair, as one skilled in the art would expect from the teaching of U.S. Pat. No. 3,231,471, the dye that would have been produced would be extremely difficult to remove from the hair. It would certainly not be easily removed by a simple wash with alkaline peroxide.

The composite hue produced by the process and compositions of the present invention is particularly desirable in the dyeing of hair. When coupled with ready removability by an alkaline peroxide wash the commercial advantages of the process and composition of the instant invention are self evident.

It should be understood that as used herein "substantially no cross reaction" means that cross reaction does not occur to the extent of blocking or interfering with the desired color formation and preventing the desired ready removability of the composite hue from the hair by a simple wash with alkaline peroxide. Moreover, unless otherwise stated, as used herein, all percentages are by weight and are based on the total weight of the composition.

The aromatic amine employed in the method of the present invention conforms to the formula I

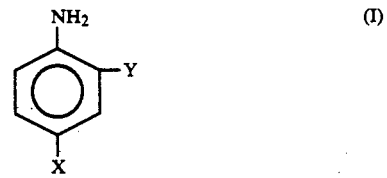

wherein Y is H, F, Cl, CN or $CF_3$ and X is OH or $NH_2$.

Examples of suitable aromatic amines include p-aminophenol, chloro-p-phenylenediamine, p-phenylenediamine and mixtures thereof.

The aldehyde employed in the composition of the present invention conforms to the following formula IIa:

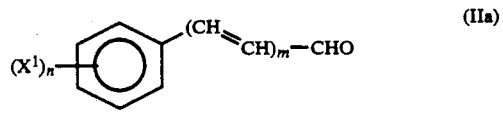

wherein $X^1$ is independently selected from the group consisting of $NH_2$, $NHR_1$, $NR_1R_2$ and OH; n is 1 or 2, provided that when n is 2 the two groups $X^1$ are meta to each other; m is 0 or 1; and $R_1$ and $R_2$ are independently alkyl of from 1 to 6 carbon atoms or hydroxy alkyl of from 1 to 6 carbon atoms.

Also suitable are hetero-aromatic aldehydes of the following formulae II b, c:

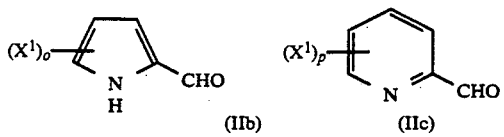

wherein $X^1$ is as previously defined, o is 0 or 1, and p is 0 or 1.

Suitable aldehydes include for example, p-dimethylaminobenzaldehyde, p-dimethylaminocinnamaldehyde, 2,4-dihydroxybenzaldehyde, pyrrole-2-carboxaldehyde and mixtures thereof.

Reaction of the aromatic amine of formula I with the aldehyde of formula II (a, b or c) produces yellow and red dyes. Peroxide oxidation of 2,6-dihydroxypyridine produces a blue dye. In combination, the yellow and/or red dyes and the blue dye provide a composite hue that is extremely desirable in the dyeing of hair. As stated heretofore, the color produced by such dyes is shampoo fast but is nonetheless readily removable by a short treatment with alkaline hydrogen peroxide.

The concentration of the aromatic amine of formula I and the concentration of the aldehyde of formula II needed to produce good dyeings is surprisingly low. Although more can be utilized, generally from about 0.01% to about 0.1% of each of the aromatic amine of formula I and the aldehyde of formula II are employed. The concentration of the aldehyde inside the hair should be at least as high or higher than the concentration of the aromatic amine. The 2,6-dihydroxypyridine is preferably employed in an amount of from about 0.5% to about 3%. The hydrogen peroxide is generally employed in an amount of from about 1% to about 6%.

The process of the present invention is carried out as follows:

(i) The aromatic amine of the formula I, or a cosmetically acceptable salt thereof, is dissolved in water to produce a first aqueous solution;

(ii) The aldehyde of the formula II is dissolved in water to produce a second aqueous solution;

(iii) The 2,6-dihydroxypyridine, or a cosmetically acceptable salt thereof, is dissolved in water to produce a third aqueous solution;

(iv) Hair is treated with hydrogen peroxide and with the first, second and third aqueous solutions;

(v) pH of one or more of the solutions is suitably adjusted so that the hair treatment step is carried out at a pH of from about 5 to about 7; and (vi) Contact of the hair with the solution(s) in step (iv) is maintained for a suffioient time to obtain the desired color. Generally, contact is maintained for less than 20 minutes, preferably, for less than 10 minutes.

An alternative and preferred method of carrying out the process of the present invention is as follows:

(i) The aromatic amine of the formula I, or a cosmetically acceptable salt thereof; the aldehyde of the formula II; the 2,6-dihydroxypyridine, or a cosmetically acceptable salt thereof; and the hydrogen peroxide are dissolved in a reaction medium containing water;

(ii) The pH of the reaction medium is adjusted to from about 5 to about 7;

(iii) Hair is treated with the pH adjusted reaction medium; and (iv) Contact of the hair with the pH adjusted reaction medium is maintained for a sufficient time to obtain the desired color. Generally, contact is maintained for less than 20 minutes, preferably for less than 10 minutes.

The process of the present invention is advantageous in that dye formation occurs inside of the hair by a chemical reaction of smaller molecules able to penetrate the hair fiber. All colors are available in a one-step dyeing procedure. Dyeings of good quality are obtained at mild conditions, not damaging to hair. Additionally, the color is easily removed when desired.

The present invention is illustrated by the Examples which follows:

EXAMPLE 1

A dye composition was prepared by dissolving 0.02% p-phenylenediamine and 0.02% p-dimethylaminobenezaldehyde, in a hydro-alcoholic solution containing 20% ethanol. The pH of the solution was adjusted to 5.5 to 6.0. White hair was dyed with the resultant composition for a period of 10 minutes whereby an orange color was imparted thereto. The orange color was removed by short wash (less than 5 minutes) with alkaline peroxide solution.

EXAMPLE 2

A dye composition was prepared by dissolving 0.02% p-aminophenol and 0.02% p-dimethylaminocinnamaldehyde, in a hydro-alcoholic solution containing 20% ethanol. The pH of the solution was adjusted to 5.5 to 6.0. White hair was dyed with the resultant composition for a period of 10 minutes whereby a red color was imparted thereto. The red color was removed by a short wash (less than 5 minutes) with alkaline peroxide solution.

EXAMPLE 3

A dye composition was prepared by dissolving 2% 2,6-dihydroxypyridine and hydrogen peroxide, in a hydro-alcoholic solution containing 20% ethanol. The pH of the solution was adjusted to 5.5 to 6.0. White hair was dyed with the resultant composition for a period of 10 minutes whereby a blue color was imparted thereto. The blue color was removed by a short wash (less than 5 minutes) with alkaline peroxide solution.

EXAMPLE 4

A dye composition was prepared by dissolving 0.02% p-aminophenol, 0.02% p-dimethylaminocinnamaldehyde, 2% 2,6-dihydroxypyridine and hydrogen peroxide, in a hydro-alcoholic solution containing 20% ethanol. The pH of the solution was adjusted to 5.5 to 6.0. White hair was dyed with the resultant composition for a period of 10 minutes whereby a violet color was imparted thereto. The violet color was removed by a short wash (less than 5 minutes) with alkaline peroxide solution.

EXAMPLE 5

A dye composition was prepared by dissolving 0.04% p-aminophenol, 0.03% p-dimethylaminobenzaldehyde and 0.01% p-dimethylaminocinnamaldehyde, in a hydro-alcoholic solution containing 20% ethanol. The pH of the solution was adjusted to 5.5 to 6.0. White hair was dyed with the resultant composition for period of 10 minutes whereby an orange color was imparted thereto. The orange color was removed by a short wash (less than 5 minutes) with alkaline peroxide solution.

EXAMPLE 6

A dye composition was prepared by dissolving 0.06% p-aminophenol, 0.06% p-dimethylaminobenzaldehyde and 2% 2,6-dihydroxypyridine, in a hydro-alcoholic solution containing 20% ethanol. The pH of the solution was adjusted to 5.5 to 6.0. White hair was dyed with the resultant composition for period of 10 minutes whereby a green color was imparted thereto. The green color was removed by a short wash (less than 5 minutes) with alkaline peroxide solution.

EXAMPLE 7

A dye composition was prepared by dissolving 0.06% p-aminophenol, 0.04% p-dimethylaminobenzaldehyde and 0.02% p-dimethylaminocinnamaldehyde, in a hydro-alcoholic solution containing 20% ethanol. The pH of the solution was adjusted to 5.5 to 6.0. White hair was dyed with the resultant composition for period of 10 minutes whereby a reddish-brown color was imparted thereto. The reddish-brown color was removed by a short wash (less than 5 minutes) with alkaline peroxide solution.

Included within the scope of the present inventions are compositions utilizable in the process of the invention. Such compositions comprise:
- an aromatic amine of the formula I or a cosmetically acceptable salt thereof, or mixtures thereof;
- an aromatic aldehyde of the formula II or a mixture of aromatic aldehydes of the formula II;
- 2,6-dihydroxypyridine or a cosmetically acceptable salt thereof;
- hydrogen peroxide; and
- a cosmetically acceptable vehicle containing water.

The pH of the composition is from about 5 to about 7, preferably the pH is from about 5.5 to about 6.0. If need be, the composition can include pH adjusting agents and one or more buffering agents to adjust and/or maintain the pH within the desired range.

The cosmetically acceptable vehicle is typically aqueous and its pH is generally 5 to 7, it can be adjusted to the desired value by means of alkalizing agents, such as ammonia, alkali metal-carbonates, alkanolamines, such as mono-, di- or tri-ethanolamine, or alkylamines, or with acidifying agents such as hydrochloric acid, sulphuric acid or citric acid.

The dyeing compositions according to the invention can also contain anionic, cationic, non-ionic and/or amphoteric surface-active agents or mixtures thereof. Among the surface-active agents which are more particularly preferred, there may be mentioned soaps; alkylbenzenesulphonates; alkylnaphthalenesulphonates; sulphates, ether-sulphates and sulphonates of fatty alcohols; quaternary ammonium salts, such as trimethylcetylammonium bromide and cetylpyridinium bromide; fatty acid diethanolamides, polyoxyethyleneated or polyglycerolated acids, alcohols and amides; and polyoxyethyleneated or polyglycerolated alkylphenols. The surface-active agents are typically present in the compositions of the instant invention in an amount of from about 0.1 to 55%, preferably from about 1 to about 40%.

The compositions can also contain organic solvents for solubilising compounds which would not otherwise be sufficiently soluble in water. Among these solvents, examples which may be mentioned are lower alkanols, such as ethanol and isopropanol glycerol, glycols or glycol ethers, such as ethylene glycol monobutyl ether, ethylene glycol, propylene glycol, and diethylene glycol monoethyl ether and monomethyl ether, and also analogous products or mixtures thereof. These solvents are preferably present in an amount of from about 1 to about 50%, more preferably from about 3 to about 30%. The compositions can also contain anionic, non-ionic, cationic or amphoteric polymers, suitably in an amount of from about 0.1 to about 5%.

The compositions according to the invention can be thickened, preferably with sodium alginate, gum arabic or cellulose derivatives, such as methylcellulose, hydroxyethylcellulose, hydroxypropylmethylcellulose and carboxymethylcellulose, or various polymers serving this purpose, in particular acrylic acid derivatives. It is also possible to use inorganic thickeners, such as bentonite. These thickeners are preferably present in amounts of from about 0.5 to about 5%, more preferably from about 0.5 to about 3%.

A particularly desirable manner of practicing the present invention and a particularly preferred composition utilizable therein are as follows:

The aromatic amine and the aromatic aldehyde are each employed as a solid material, such as a cosmetically acceptable water soluble salt thereof, for example the hydrochloride or sulfate salt. The 2,6-dihydroxypyridine is also employed as a cosmetically acceptable water soluble salt, such as the hydrochloride salt. These three components are placed in the package intended for sale with instructions that shortly before use the hydrogen peroxide (which is optionally packaged in another container accompanying the container holding the three aforementioned components or is supplied by the user) be added to the container holding the three components and the mixture be applied to hair. The process of the present invention will then take place on hair.

Desirably, the container holding the three components also contains the pH adjusting agents necessary to adjust the pH of the aqueous reaction mixture to about 5 to 7.

The amount and concentration of the peroxide should be suitably selected such that there is sufficient peroxide and sufficient water present in the reaction mixture in the package to enable the process of the present invention to proceed on hair satisfactorily.

It is also possible to utilize as a fourth component, and in lieu of the hydrogen peroxide solution, a peroxide salt, such as sodium perborate or urea peroxide. If this is done, then the process of the present invention is initiated, simply, by the user adding water to the package and applying the mixture to hair. This is a particularly preferred manner of practicing the invention.

What is claimed is:

1. A process for dyeing hair comprising:
   (a) reacting an aromatic amine selected from the group consisting of:
      (i) aromatic amines of the formula I

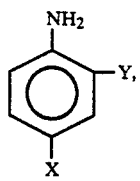

wherein Y is H, F, Cl, CN or CF$_3$ and X is OH or NH$_2$, and cosmetically acceptable salts thereof; and (ii) mixtures thereof, with an aromatic aldehyde selected from the group consisting of:

(i) aromatic aldehydes of the formula IIa

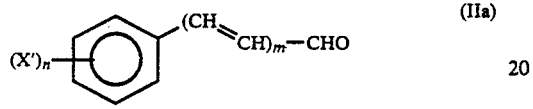

wherein X$^1$ is independently selected from the group consisting of NH$_2$, NHR$_1$, NR$_1$R$_2$ and OH; n is 1 or 2, provided that when n is 2 the two groups X$^1$ are meta to each other; m is 0 or 1; and R$_1$ and R$_2$ are independently alkyl of from 1 to 6 carbon atoms or hydroxy alkyl of from 1 to 6 carbon atoms;

(ii) heteroaromatic aldehydes of the formula II b

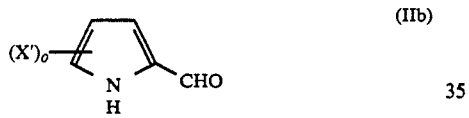

wherein X$^1$ is as defined previously, and o is 0 or 1;

(iii) heteroaromatic aldehydes of the formula IIc

wherein X$^1$ is as defined previously and p is 0 or 1; and (iv) mixtures thereof;

the reaction of the aromatic amine and the aromatic aldehyde being carried out in a reaction medium containing water;

(b) reacting 2,6-dihydroxypyridine, or a cosmetically acceptable salt thereof, with hydrogen peroxide, in a reaction medium containing water;

reacting step (a) and reacting step (b) being carried out together in a common reaction medium;

(c) adjusting the pH of the common reaction medium to about 5 to 7; and (d) applying the common reaction medium, after adjustment of its pH, to hair to be dyed for a sufficient time and in a sufficient amount to dye same whereby substantially no cross reaction occurs on the hair between reactants of step (a) and reactants of step (b).

2. The process as claimed in claim 1, wherein the aromatic aldehyde is selected from the group consisting of p-dimethylaminobenzaldehyde, p-dimethylaminocinnamaldehyde, 2,4-dihydroxybenzaldehyde, pyrrole-2-carboxaldehyde and mixtures thereof; and the aromatic amine is selected from the group consisting of p-phenylenediamine, p-aminophenol, chloro-p-phenylenediamine, and mixtures thereof.

3. A hair dye composition comprising (a) an aromatic amine selected from the group consisting of:

(i) aromatic amines of the formula I

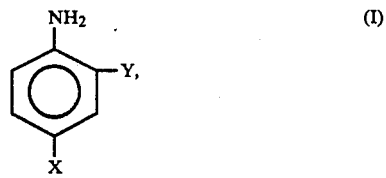

wherein Y is H, F, Cl, CN or CF$_3$ and X is OH or NH$_2$, and cosmetically acceptable salts of the amines of formula I; and (ii) mixtures thereof;

(b) an aromatic aldehyde selected from the group consisting of:

(i) aromatic aldehydes of the formula IIa

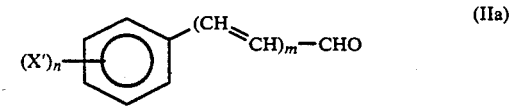

wherein X$^1$ is independently selected from the group consisting of NH$_2$, NHR$_1$, NR$_1$R$_2$ and OH; n is 1 or 2, provided that when n is 2 the two groups X$^1$ are meta to each other; m is 0 or 1; and R$_1$ and R$_2$ are independently alkyl of from 1 to 6 carbon atoms or hydroxy alkyl of from 1 to 6 carbon atoms;

(ii) heteroaromatic aldehydes of the formula II b

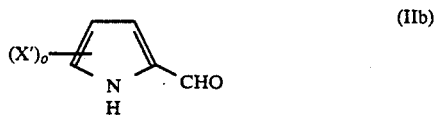

wherein X$^1$ is as defined previously and o is 0 or 1;

(iii) heteroaromatic aldehydes of the formula c

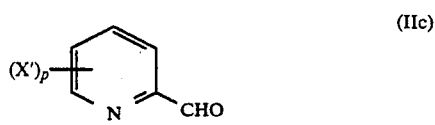

wherein X$^1$ is as defined previously and p is 0 or 1; and (iv) mixtures thereof;

(c) 2,6-dihydroxypyridine;

(d) hydrogen peroxide; and (e) a cosmetically acceptable vehicle containing water;

the aromatic amine, aromatic aldehyde 2,6-dihydroxypyridine and hydrogen peroxide being dissolved in the vehicle in respective amounts such that the aromatic amine and the aromatic aldehyde co-react in a first reaction to produce a first dye on hair and the 2,6-dihydroxypyridine and hydrogen peroxide co-react in a second reaction to produce a second dye on hair;

the composition when applied to hair, producing on the hair substantially no cross-reaction products resulting from cross-reaction of a reactant of the first reaction with a reactant of the second reaction on hair; the first dye and second dye producing on hair treated with the composition a composite hue which is readily removable by an alkaline peroxide wash.

4. The composition, as claimed in claim 3, wherein the aromatic aldehyde is selected from the group consisting of p-dimethylaminobenzaldehyde, p-dimethylaminoccinnamaldehyde, 2,4-dihydroxybenzaldehyde, pyrrole-2-carboxaldehyde and mixtures thereof; and the aromatic amine is selected from the group consisting of p-phenylenediamine, p-aminophenol, chloro-p-phenylenediamine, and mixtures thereof.

5. A hair dye system comprising
(A) a first container, the first container containing as a dry blend
(a) an aromatic amine selected from the group consisting of:
(i) aromatic amines of the formula I

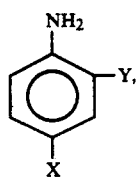

wherein Y is H, F, Cl, CN or $CF_3$ and X is OH or $NH_2$, and cosmetically acceptable salts of the amines of formula I; and
(ii) mixtures thereof; with
(b) an aromatic aldehyde selected from the group consisting of:
(i) aromatic aldehydes of the formula IIa

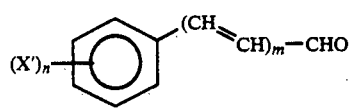

wherein $X^1$ is independently selected from the group consisting of $NH_2$, $NHR_1$, $NR_1R_2$ and OH; n is 1 or 2, provided that when n is 2 the two groups $X^1$ are meta to each other; m is 0 or 1; and $R_1$ and $R_2$ are independently alkyl of from 1 to 6 carbon atoms or hydroxy alkyl of from 1 to 6 carbon atoms
(ii) heteroaromatic aldehydes of the formula II b

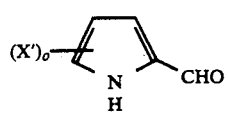

wherein $X^1$ is as defined previously and o is 0 or 1;
(iii) heteroaromatic aldehydes of the formula IIc

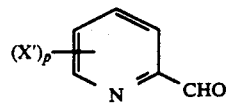

wherein $X^1$ is as defined previously and p is 0 or 1; and
(iv) mixtures thereof;
(c) 2,6-dihydroxypyridine or a cosmetically acceptable salt thereof;
(B) a second container, the second container containing hydrogen peroxide and sufficient water so that when the contents of the second container and the contents of the the first container are mixed and applied to hair the aromatic amine will react with the aromatic aldehyde in a first reaction and the 2,6-dihydroxypyridine, or salt thereof, will react with the hydrogen peroxide in a second reaction, the first and the second reactions occurring simultaneously on hair with substantially no crossreaction between reactants of the first reaction and reactants of the second reaction; and
(C) written indicia instructing that the contents of the first container and the contents of the second container be mixed shortly before application to hair whereby an aqueous reaction mixture is produced.

6. The system as claimed in claim 5, further containing, in either the first container or the second container or in each of the first and the second containers, sufficient pH adjusting material so that the aqueous reaction mixture has a pH of about 5 to 7.

7. A hair dye system comprising
(A) a first container, the first container containing as a dry blend
(a) an aromatic amine selected from the group consisting of:
(i) aromatic amines of the formula I

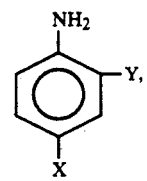

wherein Y is H, F, Cl, CN or $CF_3$ and X is OH or $NH_2$; and cosmetically acceptable salts of the amines of formula I; and
(ii) mixtures thereof; with
(b) an aromatic aldehyde selected from the group consisting of:
(i) aromatic aldehydes of the formula IIa

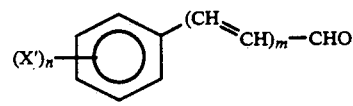

wherein $X^1$ is independently selected from the group consisting of $NH_2$, $NHR_1$, $NR_1R_2$ and OH; n is 1 or 2, provided that when n is 2, the two groups $X^1$ are meta to each other; m is 0 or 1; and $R_1$ and $R_2$ are independently alkyl of from 1 to 6 carbon atoms or hydroxy alkyl of from 1 to 6 carbon atoms;

(ii) heteroaromatic aldehydes of the formula II b

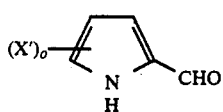
(IIb)

wherein $X^1$ is as defined previously and o is 0 or 1; and (iii) heteroaromatic aldehydes of the formula IIc

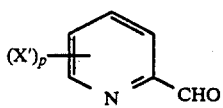
(IIc)

wherein $X^1$ is as defined previously and p is 0 or 1;

(c) 2,6-dihydroxypyridine or a cosmetically acceptable salt thereof;

the aromatic amine, the aromatic aldehyde and the 2,6-dihydroxypyridine each being independently selected from the group consisting of solid water soluble cosmetically acceptable salts; and (d) a solid water soluble peroxide salt; and (B) a second container, the second container containing a sufficient amount of water so that when the contents of the second container and the contents of the first container are mixed and applied to hair, the aromatic amine reacts with the aromatic aldehyde in a first reaction and the 2,6-dihydroxypyridine, or salt thereof, reacts with the peroxide salt in a second reaction and the first and the second reactions occur simultaneously on hair with substantially no cross-reaction between reactants of the first reaction and the reactants of the second reaction;

(C) written indicia instructing that the contents of the first container and the contents of the second container be mixed shortly before application to hair.

8. The system as claimed in claim 7, further containing, in either the first container or the second container or in each of the first and the second containers, sufficient pH adjusting material so that the aqueous reaction medium has a pH of about 5 to 7.

* * * * *